US012458722B1

(12) United States Patent
Brown et al.

(10) Patent No.: US 12,458,722 B1
(45) Date of Patent: Nov. 4, 2025

(54) SYSTEMS, METHOD, AND DEVICES FOR DISPENSING VOLATILE LIQUIDS

(71) Applicant: Fresh Products, Inc., Perrysburg, OH (US)

(72) Inventors: Douglas S. Brown, Toledo, OH (US); Jeffrey A. Smith, Perrysburg, OH (US)

(73) Assignee: Fresh Products, Inc., Perrysburg, OH (US)

( * ) Notice: Subject to any disclaimer, the term of this patent is extended or adjusted under 35 U.S.C. 154(b) by 394 days.

(21) Appl. No.: 17/185,291

(22) Filed: Feb. 25, 2021

Related U.S. Application Data

(60) Provisional application No. 62/982,334, filed on Feb. 27, 2020.

(51) Int. Cl.
*A61L 9/14* (2006.01)
*B05B 7/04* (2006.01)
*B05B 7/08* (2006.01)
*B05B 7/24* (2006.01)

(52) U.S. Cl.
CPC .............. *A61L 9/14* (2013.01); *B05B 7/0483* (2013.01); *B05B 7/0869* (2013.01); *A61L 2209/134* (2013.01); *B05B 7/2491* (2013.01)

(58) Field of Classification Search
CPC . A61L 9/14; A61L 9/032; A61L 9/035; A61L 9/122; A61L 9/125; B05B 7/0869
See application file for complete search history.

(56) References Cited

U.S. PATENT DOCUMENTS 2,069,179 A 1/1937 Dunaway
2,243,151 A 5/1941 Fuld et al.
2,251,058 A 7/1941 Kirkman
2,642,310 A 6/1953 Meek et al.
2,657,090 A 10/1953 Meek
2,707,930 A 5/1955 Miles
2,794,676 A 6/1957 D'Agostino
2,908,473 A 10/1959 Snyder
2,925,202 A 2/1960 Stevens
3,104,816 A 9/1963 Jaffe
3,239,145 A 3/1966 Russo
3,269,605 A 8/1966 Silver
3,288,420 A 11/1966 Maruoka
3,375,538 A 4/1968 Mains et al.
3,380,632 A 4/1968 Wilson
(Continued)

FOREIGN PATENT DOCUMENTS

CH 296864 2/1954
CN 215386206 U 1/2022
(Continued)

OTHER PUBLICATIONS

Advertisements dated Sep. 20, 1989 and Jan. 20, 1998 and updated advertising materials showing a combination soap and air freshener dispenser.

*Primary Examiner* — Timothy C Cleveland

(74) *Attorney, Agent, or Firm* — Knobbe, Martens, Olson & Bear, LLP

(57) ABSTRACT

A volatile liquid dispenser includes a chamber for holding a supply of volatile liquid; a compressor configured to force a portion of the supply of volatile liquid out of the chamber and through an outlet; and a fan configured to force the portion of the supply of volatile liquid exiting the outlet into the surrounding air and away from the outlet.

23 Claims, 6 Drawing Sheets

(56) References Cited

U.S. PATENT DOCUMENTS

| | | | |
|---|---|---|---|
| 3,522,935 | A | 8/1970 | Lewis |
| 3,729,553 | A | 4/1973 | Gold et al. |
| 3,833,149 | A | 9/1974 | Iozzio |
| 3,902,637 | A | 9/1975 | Scheeler |
| 3,993,444 | A | 11/1976 | Brown |
| 4,039,104 | A | 8/1977 | Mijares, Jr. et al. |
| 4,065,261 | A | 12/1977 | Fukada |
| 4,067,692 | A | 1/1978 | Farris |
| 4,154,375 | A | 5/1979 | Bippus |
| 4,252,547 | A | 2/1981 | Johnson |
| 4,294,778 | A | 10/1981 | DeLuca |
| 4,323,193 | A | 4/1982 | Compton et al. |
| 4,570,827 | A | 2/1986 | Roggenburg, Jr. et al. |
| 4,580,581 | A | 4/1986 | Reece et al. |
| 4,636,328 | A | 1/1987 | Flynn et al. |
| 4,709,425 | A | 12/1987 | Bavaveas |
| 4,741,461 | A | 5/1988 | Williamson et al. |
| 4,743,406 | A | 5/1988 | Steiner et al. |
| 4,808,347 | A | 2/1989 | Dawn |
| 4,821,923 | A | 4/1989 | Skorka |
| 4,881,652 | A | 11/1989 | Schiemann |
| 4,903,584 | A | 2/1990 | Styles |
| 4,905,112 | A | 2/1990 | Rhodes |
| 4,921,131 | A | 5/1990 | Binderbauer et al. |
| 4,921,636 | A | 5/1990 | Traas |
| 4,946,070 | A | 8/1990 | Albert et al. |
| 4,946,072 | A | 8/1990 | Albert et al. |
| 4,955,508 | A | 9/1990 | Campanna et al. |
| 4,967,935 | A | 11/1990 | Celest |
| RE33,864 | E | 3/1992 | Steiner et al. |
| 5,102,015 | A | 4/1992 | Barnard et al. |
| 5,115,945 | A | 5/1992 | Ruck |
| 5,147,582 | A | 9/1992 | Holzner, Sr. et al. |
| 5,165,603 | A | 11/1992 | Hahn |
| 5,167,877 | A | 12/1992 | Pai |
| 5,178,327 | A | 1/1993 | Palamand et al. |
| 5,180,107 | A | 1/1993 | Lindauer |
| 5,186,360 | A | 2/1993 | Mease et al. |
| 5,223,182 | A | 6/1993 | Steiner et al. |
| 5,238,187 | A | 8/1993 | Zlotnik et al. |
| 5,265,772 | A | 11/1993 | Bartasevich et al. |
| 5,284,272 | A | 2/1994 | Wei |
| 5,367,716 | A | 11/1994 | Huang |
| 5,379,917 | A | 1/1995 | Brown et al. |
| 5,477,640 | A | 12/1995 | Holtkamp, Jr. |
| 5,487,877 | A | 1/1996 | Choi |
| 5,595,324 | A | 1/1997 | Brown et al. |
| 5,690,255 | A | 11/1997 | White |
| 5,695,692 | A | 12/1997 | Kennedy |
| 5,791,525 | A | 8/1998 | Fan |
| 5,799,826 | A | 9/1998 | Brown et al. |
| 5,805,768 | A | 9/1998 | Schwartz et al. |
| 5,842,675 | A | 12/1998 | Davitt |
| 5,898,475 | A | 4/1999 | Martin |
| 5,911,362 | A | 6/1999 | Wood et al. |
| D414,253 | S | 9/1999 | Kobayashi et al. |
| 6,062,425 | A | 5/2000 | Brown et al. |
| 6,249,919 | B1 | 6/2001 | Bryson, Jr. et al. |
| 6,254,065 | B1 | 7/2001 | Ehrensperger et al. |
| 6,318,600 | B1 | 11/2001 | Winnett et al. |
| 6,357,726 | B1 | 3/2002 | Watkins |
| D459,950 | S | 7/2002 | Bush et al. |
| 6,536,746 | B2 | 3/2003 | Watkins |
| 6,569,387 | B1 | 5/2003 | Furner et al. |
| 6,581,915 | B2 | 6/2003 | Bartsch et al. |
| 6,619,559 | B2 | 9/2003 | Wohrle |
| 6,655,604 | B2 | 12/2003 | Tuttobene, Jr. |
| 6,713,024 | B1 | 3/2004 | Arnell et al. |
| 6,769,631 | B2 | 8/2004 | Brown |
| 6,783,117 | B2 | 8/2004 | Wohrle |
| 6,786,474 | B2 | 9/2004 | Watkins et al. |
| 6,834,847 | B2 | 12/2004 | Bartsch et al. |
| 6,913,733 | B2 | 7/2005 | Hardy et al. |
| D508,285 | S | 8/2005 | Velicescu |
| 6,994,328 | B2 | 2/2006 | Watkins et al. |
| 7,011,795 | B2 | 3/2006 | Thompson et al. |
| 7,036,800 | B2 | 5/2006 | Ellis |
| 7,070,172 | B2 | 7/2006 | Fabrega et al. |
| 7,160,515 | B2 | 1/2007 | Murdell et al. |
| 7,188,780 | B2 | 3/2007 | Martens, III |
| 7,188,783 | B2 | 3/2007 | Ivey et al. |
| 7,223,361 | B2 | 5/2007 | Kvietok et al. |
| D547,429 | S | 7/2007 | Yoo et al. |
| 7,344,123 | B2 | 3/2008 | Pankhurst et al. |
| D570,464 | S | 6/2008 | Normark et al. |
| 7,389,943 | B2 | 6/2008 | Jaworski |
| 7,484,716 | B2 | 2/2009 | Ford Morie et al. |
| 7,600,697 | B2 | 10/2009 | Bankers et al. |
| 7,610,118 | B2 | 10/2009 | Schramm et al. |
| 7,622,073 | B2 | 11/2009 | Schramm et al. |
| D606,642 | S | 12/2009 | Weggelaar et al. |
| 7,651,077 | B1 | 1/2010 | Rosener et al. |
| 7,691,336 | B2 | 4/2010 | Westring |
| D618,328 | S | 6/2010 | Chan et al. |
| 7,748,687 | B2 | 7/2010 | Pankhurst et al. |
| 7,857,236 | B2 | 12/2010 | Zlotnik et al. |
| 7,922,104 | B2 | 4/2011 | Zlotnik et al. |
| 7,930,068 | B2 | 4/2011 | Robert et al. |
| 7,942,388 | B2 | 5/2011 | Suissa et al. |
| 7,981,367 | B2 | 7/2011 | Kvietok et al. |
| 8,016,207 | B2 | 9/2011 | Kvietok et al. |
| 8,048,379 | B2 | 11/2011 | Sassoon |
| 8,061,628 | B1 | 11/2011 | Kvietok et al. |
| 8,074,970 | B2 | 12/2011 | Pankhurst et al. |
| 8,119,064 | B2 | 2/2012 | Woo et al. |
| D664,246 | S | 7/2012 | Irvin et al. |
| 8,210,448 | B2 | 7/2012 | Kvietok et al. |
| 8,220,782 | B2 | 7/2012 | Hepple |
| 8,349,251 | B2 | 1/2013 | Woo et al. |
| 8,414,834 | B2 | 4/2013 | Gorman |
| 8,469,293 | B2 | 6/2013 | Doty et al. |
| 8,485,454 | B1 | 7/2013 | Irvin et al. |
| 8,603,397 | B2 | 12/2013 | Gruenbacher et al. |
| 8,870,165 | B2 | 10/2014 | Scolari |
| 8,881,999 | B2 | 11/2014 | Blaylock et al. |
| 8,899,493 | B2 | 12/2014 | Kim et al. |
| 9,265,853 | B2 | 2/2016 | Scott et al. |
| D753,809 | S | 4/2016 | Schlegel |
| D754,316 | S | 4/2016 | Yasuoka et al. |
| D754,317 | S | 4/2016 | Yasuoka |
| 9,364,575 | B2 | 6/2016 | Habbel |
| D764,040 | S | 8/2016 | Cho et al. |
| D784,504 | S | 4/2017 | Kim et al. |
| D784,506 | S | 4/2017 | Kim et al. |
| D784,507 | S | 4/2017 | Kim et al. |
| 9,717,815 | B2 | 8/2017 | Peterson et al. |
| D798,430 | S | 9/2017 | Nord et al. |
| D804,005 | S | 11/2017 | Spear et al. |
| D831,186 | S | 10/2018 | Tamras et al. |
| D837,355 | S | 1/2019 | Gunnefur |
| D838,354 | S | 1/2019 | Farone |
| D858,727 | S | 9/2019 | Uchiyama et al. |
| D858,732 | S | 9/2019 | Hyon et al. |
| D900,291 | S | 10/2020 | Brown et al. |
| D935,593 | S | 11/2021 | Andres |
| D993,377 | S | 7/2023 | Andres |
| 11,813,378 | B2 | 11/2023 | Becker |
| D1,036,638 | S | 7/2024 | Brown et al. |
| 12,064,778 | B2 | 8/2024 | Hoffman et al. |
| 2002/0066798 | A1 | 6/2002 | Laudamiel-Pellet et al. |
| 2002/0068009 | A1 | 6/2002 | Laudamiel-Pellet et al. |
| 2002/0068010 | A1 | 6/2002 | Laudamiel-Pellet et al. |
| 2003/0175148 | A1 | 9/2003 | Kvietok et al. |
| 2004/0007787 | A1 | 1/2004 | Kvietok et al. |
| 2004/0033171 | A1 | 2/2004 | Kvietok et al. |
| 2004/0265164 | A1 | 12/2004 | Woo et al. |
| 2005/0147523 | A1 | 7/2005 | Laudamiel-Pellet et al. |
| 2005/0147539 | A1 | 7/2005 | Laudamiel-Pellet et al. |
| 2005/0214158 | A1 | 9/2005 | Kvietok et al. |
| 2005/0265904 | A1 | 12/2005 | Hardy et al. |
| 2006/0067859 | A1 | 3/2006 | Laudamiel-Pellet et al. |
| 2006/0081721 | A1 | 4/2006 | Caserta et al. |
| 2006/0145368 | A1* | 7/2006 | Thomas .................... A61L 9/12 261/118 |

(56) References Cited

U.S. PATENT DOCUMENTS

| | | | |
|---|---|---|---|
| 2006/0153744 | A1 | 7/2006 | Thompson et al. |
| 2006/0196100 | A1 | 9/2006 | Laudamiel-Pellet et al. |
| 2006/0226251 | A1 | 10/2006 | Helf et al. |
| 2007/0181706 | A1 | 8/2007 | Yeh et al. |
| 2008/0038156 | A1 | 2/2008 | Jaramillo |
| 2008/0164337 | A1 | 7/2008 | Brown et al. |
| 2008/0191370 | A1 | 8/2008 | Pankhurst et al. |
| 2008/0245890 | A1 | 10/2008 | Lockwood et al. |
| 2009/0001213 | A1 | 1/2009 | Looft |
| 2009/0159719 | A1 | 6/2009 | Millet |
| 2009/0173799 | A1 | 7/2009 | Litten-Brown et al. |
| 2009/0200399 | A1 | 8/2009 | McGee et al. |
| 2009/0212124 | A1 | 8/2009 | Kenny |
| 2009/0218413 | A1 | 9/2009 | Withers |
| 2010/0038443 | A1 | 2/2010 | Pankhurst et al. |
| 2010/0090022 | A1 | 4/2010 | Hayashida |
| 2010/0187327 | A1 | 7/2010 | Irvin |
| 2010/0221143 | A1 | 9/2010 | Broncano Atencia et al. |
| 2010/0272599 | A1 | 10/2010 | Broncano Atencia et al. |
| 2010/0320282 | A1 | 12/2010 | Sissom |
| 2011/0089252 | A1 | 4/2011 | Rosener et al. |
| 2011/0114746 | A1 | 5/2011 | Habbel |
| 2011/0290903 | A1 | 12/2011 | Nagano et al. |
| 2012/0000989 | A1 | 1/2012 | Bordier |
| 2012/0018527 | A1 | 1/2012 | Duddington et al. |
| 2012/0126024 | A1 | 5/2012 | Boyd et al. |
| 2012/0205460 | A1 | 8/2012 | Franks |
| 2012/0261484 | A2 | 10/2012 | Blaylock et al. |
| 2014/0001286 | A1 | 1/2014 | Scott et al. |
| 2014/0079586 | A1* | 3/2014 | Shapiro ............... A01M 1/2072 422/4 |
| 2015/0108243 | A1 | 4/2015 | Bourne |
| 2017/0067608 | A1 | 3/2017 | Patton |
| 2017/0072087 | A1* | 3/2017 | Tai ............................ A61L 9/14 |
| 2017/0216474 | A1 | 8/2017 | Kelsen |
| 2018/0154035 | A1 | 6/2018 | Joshi et al. |
| 2019/0307913 | A1* | 10/2019 | Hsiao .................. F21V 33/0024 |
| 2020/0330637 | A1* | 10/2020 | Chang ................... B01F 23/213 |
| 2021/0069371 | A1 | 3/2021 | Mushtaq et al. |
| 2022/0088256 | A1 | 3/2022 | Robinson et al. |
| 2022/0160924 | A1 | 5/2022 | Connors et al. |
| 2022/0395601 | A1 | 12/2022 | Trias Lafuente et al. |
| 2023/0311142 | A1 | 10/2023 | Gao et al. |

FOREIGN PATENT DOCUMENTS

| | | | |
|---|---|---|---|
| CN | 114533932 | A | 5/2022 |
| CN | 217403557 | U | 9/2022 |
| DE | 461572 | | 6/1928 |
| DE | 3239511 | | 4/1984 |
| DE | 102012016994 | | 3/2013 |
| FR | 2741807 | | 6/1997 |
| JP | 4625569 | B2 | 2/2011 |
| KR | 1020220071484 | A | 5/2022 |
| WO | WO 00/12143 | | 3/2000 |
| WO | WO 02/34414 | | 5/2002 |
| WO | WO 2024/149900 | A1 | 1/2024 |

* cited by examiner

SYSTEMS, METHOD, AND DEVICES FOR DISPENSING VOLATILE LIQUIDS

CROSS-REFERENCE TO RELATED APPLICATIONS

This application claims the benefit of U.S. Provisional Application No. 62/982,334, titled DISPENSER, filed Feb. 27, 2020, the entirety of which is hereby incorporated by reference herein.

BACKGROUND

Field

This disclosure relates generally to dispensers, and more specifically to dispensers for fragrances and other volatile liquids.

SUMMARY

Disclosed herein are various embodiments of dispensers and dispensing techniques used to efficiently, effectively, and cleanly disperse atomized liquid fragrance throughout an area, such as a room, bathroom, office, and/or the like. The dispensers and dispensing techniques disclosed herein comprise embodiments that atomize a liquid fragrance, such as by using a venturi atomizer mechanism, and disperse the atomized liquid fragrance using forced air, such as from a fan, ducted fan, compressed air source, and/or the like. The combination of atomizing the liquid fragrance with a venturi atomizer and dispersing the atomized liquid fragrance using forced air provides various benefits, such as, for example, reducing buildup of residue on the atomizer outlet, reducing maintenance requirements, reducing collection of and/or buildup of atomized fragrance on surfaces near the dispenser, dispersing the fragrance over a larger area to enable less concentration of fragrance in only an area immediately adjacent the dispenser, and/or the like.

According to some embodiments, a volatile liquid dispensing system comprises: a reservoir for holding a supply of volatile liquid (such as fragrance, sanitizer, and/or the like); a pressurized gas (such as compressed air) source; an atomizer comprising a chamber, an outlet nozzle fluidly coupleable to the chamber, and a venturi assembly positioned within the chamber, wherein the venturi assembly comprises a first orifice fluidly coupleable to the pressurized gas source through a flow path that includes a venturi nozzle, and a second orifice fluidly coupleable to the reservoir, wherein the atomizer is configured to cause, responsive to pressurized gas from the pressurized gas source flowing through the venturi nozzle, extraction of a portion of the supply of volatile liquid through the second orifice, atomization of the portion of the supply of volatile liquid within the chamber and/or the outlet nozzle, and expelling of the atomized liquid through the outlet nozzle; an electrical power source; and a fan configured to be powered by the electrical power source in order to disperse the atomized liquid expelled through the outlet nozzle.

In some embodiments, the pressurized gas source comprises a compressor configured to be powered by the electrical power source. In some embodiments, the pressurized gas source comprises a chamber containing pressurized fluid. In some embodiments, the electrical power source comprises a battery. In some embodiments, the electrical power source comprises a connection to receive power from an external AC power source. In some embodiments, the fan is positioned adjacent the outlet nozzle. In some embodiments, the fragrance dispensing system further comprises a duct configured to transfer air from the fan to a position adjacent the outlet nozzle. In some embodiments, the fan can create a flow rate of 300-1000 cubic feet per minute. In some embodiments, the fragrance dispensing system further comprises a controller configured to selectively activate and deactivate the compressed air source and fan. In some embodiments, the controller is configured to deactivate the pressurized gas source prior to deactivating the fan. In some embodiments, the fragrance dispensing system further comprises a housing that contains at least the reservoir, pressurized gas source, atomizer, and fan. In some embodiments, the volatile liquid dispensing system further comprises a second reservoir for holding a supply of a second volatile liquid, wherein the atomizer is further configured to cause extraction of a portion of the supply of the second volatile liquid, atomization of the portion of the supply of the second volatile liquid within the chamber and/or outlet nozzle, and expelling of the atomized second liquid through the outlet nozzle.

According to some embodiments, a dispenser comprises: a chamber for holding a supply of volatile liquid (such as fragrance, sanitizer, and/or the like); a compressor configured to force a portion of the supply of volatile liquid out of the chamber and through an outlet; and a fan configured to force the portion of the supply of volatile liquid exiting the outlet into the surrounding air and away from the outlet.

In some embodiments, the fan can create a flow rate of 300-1000 cubic feet per minute. In some embodiments, the dispenser further comprises a flow path which creates a venturi. In some embodiments, the compressor is configured to force compressed gas through the flow path to create a pressure differential that causes the portion of the supply of volatile liquid to be extracted from the chamber. In some embodiments, the dispenser further comprises a controller configured to deactivate the compressor prior to deactivating the fan.

According to some embodiments, a method of dispensing volatile liquid (such as fragrance, sanitizer, and/or the like) comprises: providing a chamber for holding a supply of volatile liquid; forcing a portion of the supply of volatile liquid out of the chamber and through an outlet by entraining the portion of the supply of volatile liquid into a flow path with compressed gas; and dispersing the portion of the supply of volatile liquid exiting the chamber through the outlet into the surrounding air and away from the outlet with a fan.

In some embodiments, dispersing the portion of the supply of volatile liquid exiting the chamber through the outlet into the surrounding air and away from the outlet with a fan comprises using the fan to create a flow rate of 300-1000 cubic feet per minute. In some embodiments, the forcing of the portion of the supply of volatile liquid comprises utilizing a venturi effect. In some embodiments, the forcing of the portion of the supply of volatile liquid further comprises atomizing the portion of the supply of volatile liquid.

For purposes of this summary, certain aspects, advantages, and novel features of the inventions are described herein. It is to be understood that not necessarily all such advantages may be achieved in accordance with any particular embodiment of the inventions. Thus, for example, those skilled in the art will recognize that the inventions may be embodied or carried out in a manner that achieves one advantage or group of advantages as taught herein without necessarily achieving other advantages as may be taught or suggested herein

BRIEF DESCRIPTION OF THE DRAWINGS

The foregoing and other features, aspects, and advantages of the present disclosure are described in detail below with reference to the drawings of various embodiments, which are intended to illustrate and not to limit the disclosure. The features of some embodiments of the present disclosure, which are believed to be novel, will be more fully disclosed in the following detailed description. The following detailed description may best be understood by reference to the accompanying drawings wherein the same numbers in different drawings represents the same parts. All drawings are schematic and are not intended to show any dimension to scale. The drawings comprise the following figures in which.

DETAILED DESCRIPTION

Figure 1B:
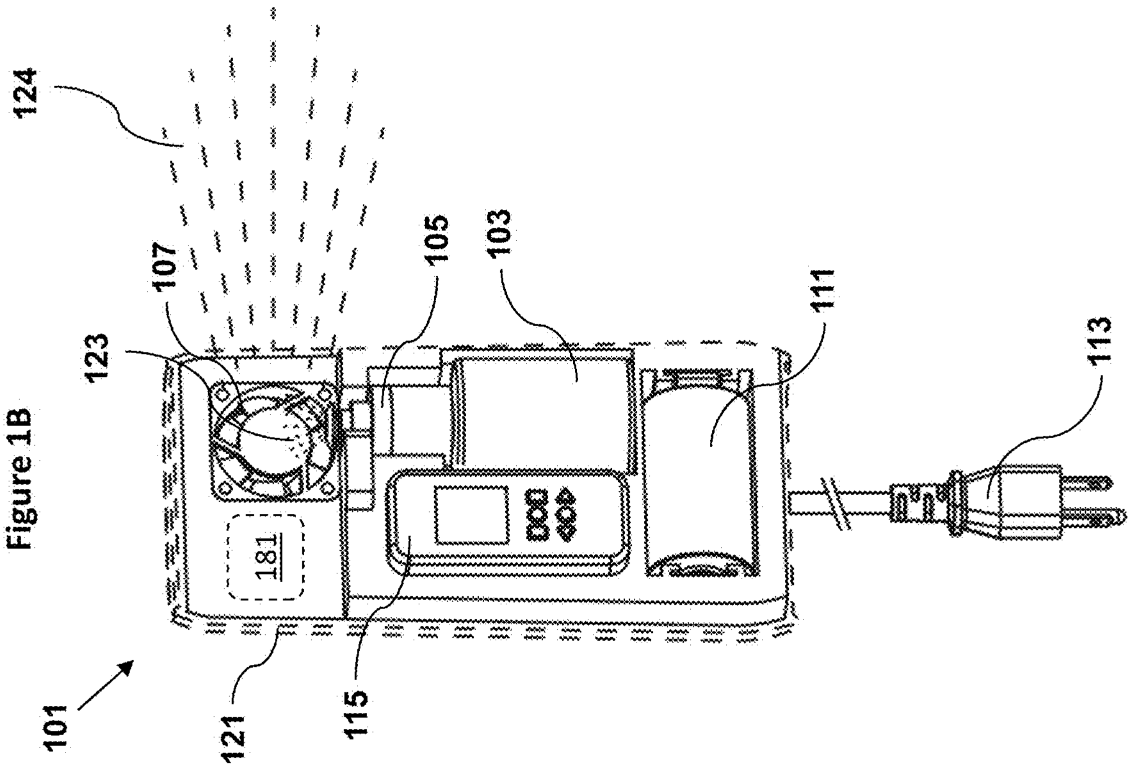
FIG. 1B is a perspective view illustrating the fragrance dispenser of FIG. 1A dispersing an atomized fragrance.

Although several embodiments, examples, and illustrations are disclosed below, it will be understood by those of ordinary skill in the art that the inventions described herein extend beyond the specifically disclosed embodiments, examples, and illustrations and include other uses of the inventions and obvious modifications and equivalents thereof. Embodiments of the inventions are described with reference to the accompanying figures, wherein like numerals refer to like elements throughout. These drawings are considered to be a part of the entire description of some embodiments of the inventions. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Disclosed herein are various embodiments of dispensers and dispensing techniques for atomizing a volatile liquid, such as a fragrance, and dispersing the atomized liquid throughout an area, such as a room, bathroom, office space, and/or the like. A dispenser as disclosed herein may comprise an electrically powered device that atomizes a liquid fragrance using a venturi atomizer mechanism. The venturi atomizer mechanism may be supplied with compressed air from a compressed air source, such as an electrically powered compressor pump or other source of compressed air. The compressed air may be passed through a venturi mechanism that causes liquid fragrance to be drawn into the atomizer, atomized into small particles that form a mist, and expelled out through an outlet nozzle or orifice of the atomizer. The dispenser may further comprise a source of forced air, such as a fan, a ducted fan, and/or the like, that blows air past the outlet of the atomizer to cause the atomized fragrance to be more widely dispersed about an area than if the forced air source were not used.

Some dispenser embodiments may include an internal power source, such as a battery and/or an external power source, such as a connection to an electrical outlet; a fan and a volatilizer, such as an atomizer, to disperse a volatile liquid (such as fragrance) contained in a container, such as a bottle defining a chamber, throughout a room. For example, some embodiments may be configured such that when the dispenser is in a calm environment (e.g., an enclosed space with no airflow other than airflow generated by the dispenser) and a portion of a supply of volatile liquid is atomized, at least 60% of the atomized volatile liquid travels at least 10 feet away from the dispenser. In some embodiments, at least 60% of the atomized volatile liquid travels at least 5, 10, 15, or 20 feet away from the dispenser. In some embodiments, at least 40% of the atomized volatile liquid travels at least 15 feet away from the dispenser. In some embodiments, at least 40% of the atomized volatile liquid travels at least 10, 15, 20, or 25 feet away from the dispenser. In some embodiments, at least 50% of the atomized volatile liquid travels at least twice as far as it would travel without the fan activated. In some embodiments, at least 50% of the atomized volatile liquid travels at least 2, 3, 4, 5, or more times as far as it would travel without the fan activated. The fan may desirably be an axial flow fan and desirably can generate a flow rate of at least 300 cubic feet per minute and/or over 600 feet per minute. In one configuration, the fan can create a flow rate of 300-1000 cubic feet per minute. In some configurations, the fan can create a flow rate of at least 200, 300, 400, 500, 600, 700, 800, 1000, or more cubic feet per minute. In some configurations, the fan can create a flow rate within a range bounded by any two of the above numbers. The fan may desirably rotate over 500 revolutions per minute and/or over 1000 revolutions per minute. In one configuration, the fan can rotate between 500-5000 revolutions per minute. In some configurations, the fan can rotate at a speed of at least 250, 500, 750, 1000, 1250, 1500, 1750, 2000, 2250, 2500, 2750, 3000, 3250, 3500, 3750, 4000, 4250, 4500, 4700, 5000, or more revolutions per minute. In some configurations, the fan can rotate at a speed that is within a range bounded by any two of the above numbers. The atomizer may desirably use a compressor pump, which directs a small amount of air through a flow path, which desirably defines a venturi, causing liquid material to flow through the flow path from the bottle and to be vaporized into small droplets and dispersed from the outlet of the atomizer. In some configurations, the compressor pump may be configured to output compressed air or another pressurized gas at a pressure of at least 10 psi. In some configurations, the source of pressurized gas, such as the compressor pump may be configured to output compressed air or another pressurized gas at a pressure of at least 2.5, 5, 10, 15, 20, 25, 30, 35, 40, 45, 50, 55, 60, 65, 70, 75, or more psi. In some configurations, the compressor pump may be configured to output compressed air or another pressurized gas at a pressure that is within a range bounded by any two of the above numbers. For most applications, it will be necessary or desirable for the pressurized gas to have a pressure higher than the ambient pressure. While ambient air pressure varies based on a number of factors, for purposes of this application "standard ambient pressure" is the pressure at sea level or 14.6959 psi. In some embodiments, the atomizer may be referred to as an actuator, and the liquid material may exit the top of the actuator. When the compressor pump is activated (causing the atomization of the liquid) the fan desirably starts and actively pushes the volatized liquid, which exits the actuator outward to help disperse the volatized liquid further into the room.

The devices and techniques disclosed herein, including the combination of a fan and atomizer, can provide various benefits. A drawback to currently available dispensers is the buildup of liquid and semi-solid (sticky) residue around the actuation area. For example, a fragrance may comprise one or more solid compounds dissolved in a solvent, such as water, alcohol, dioctyl adipate, di-propylene glycol, and/or the like. When the fragrance is atomized, micro-droplets are generated, and at least some of the micro-droplets may condense on the dispenser and actuator surfaces. When those micro-droplets contain dissolved solid compounds, those solids begin to harden as the solvent body evaporates, often leaving a sticky (more viscous) residual layer. One benefit enhancing the technology by combining it with a fan is to create a cleaner dispersion of the volatized liquid (e.g., by reducing buildup of residue on surfaces of the dispenser and/or surfaces around the dispenser). The fan assists the movement of the micro-droplets to prevent the liquid from settling on the surfaces and leaving a coating on tables, floors, the dispenser etc. Airflow testing has also shown that by combining the actuator with a fan that the volatized liquid will disperse better throughout the area due to the fan pushing the molecules outward throughout the room. This could also be further improved by using heat to accelerate the dispersion process. For example, some dispensers may include a heating device or element configured to heat the volatile liquid to at least 200° F. Some dispensers may include a heating device or element configured to heat the volatile liquid to at least 70° F., 80° F., 90° F., 100° F., 125° F., 150° F., 175° F., 200° F., 250° F., 300° F., 400° F., 500° F., or more. Some dispensers may include a heating device or element configured to heat the volatile liquid to within a range bounded by any of the above numbers. The distance of dispersion can be important if, for example, the volatile liquid contains active ingredients that can be more efficacious if they are dispersed more thoroughly (for example, an air sanitizing compound, antibacterial agent, and/or the like).

As discussed above, dispersing an atomized fragrance using a fan or other source of forced air can help to transfer the fragrance over a larger space and/or help to reduce the concentration of the fragrance in the area immediately around the dispenser. Further, the fan can help to reduce buildup of residue on the atomizer outlet, which would otherwise lead to eventually clogging the atomizer, reducing the effectiveness of the atomizer, requiring cleaning or maintenance of the atomizer, and/or the like. Similarly, dispersing the atomized fragrance over a larger area, and thus reducing the concentration of atomized fragrance in the air immediately surrounding the dispenser, can help to avoid or reduce buildup of fragrance residue on surfaces near the dispenser, such as tables, floors, walls, desks, and/or the like.

Some embodiments of dispensers disclosed herein may be electrically powered, such as using an internal stored energy source, such as a battery, capacitor, supercapacitor, and/or the like, using an externally supplied power source, such as via an AC outlet, and/or a combination thereof. In some embodiments, the system can be configured to reduce power usage and/or to use power more efficiently in order to, for example, extend the life of a stored energy source such as a battery. For example, dispersing the atomized fragrance over a wider area than if a fan were not used can help to extend the time between dispensings. For example, if fragrance were not widely dispersed and were significantly less concentrated on one side of the room than another side of the room, the fragrance may need to be dispersed more frequently to ensure the side of the room with the lower concentration of fragrance maintains an adequate level of fragrance. With a design as disclosed herein, however, which can help to more evenly distribute the concentration of fragrance, less frequent actuation of the dispenser may be possible while maintaining a similar minimum level of concentration in various portions of the room.

Another example of how power savings may be achieved with systems disclosed herein is that the dispenser may comprise a controller that independently controls the activation, deactivation, and/or speed of an air compressor that supplies air to the atomizer and a fan that supplies a source of forced air for dispersing the atomized mist. For example, there may be a known or derivable delay between the time the compressor is activated and the time atomized mist first starts being output from the outlet of the atomizer. In some configurations, such a delay may be at least, for example, 0.250, 0.500, 0.750, 1, 2, 3, 4, 5, 6, 7, 8, 9, 10, 20, 30, or more seconds. In some configurations, such a delay may be within a range bounded by any of the above numbers. For example, the delay may between 0.250 seconds and 30 seconds or 0.500 seconds and 2 seconds. The controller in some systems may be configured to start or activate the compressor first, and then delay for such a period of time, or a period of time having a relationship to such a period of time, before starting the fan. For example, the configured delay may be less than the delay between the time the compressor is activated and the time the atomized mist first starts being output from the atomizer, because it may be desirable to take into account the amount of time the fan takes to get up to its operating speed, its flow rate, and/or the like. For example, the configured delay may in some embodiments be less than the known or derivable delay by at least 0.100, 0.250, 0.500, 0.750, 1, 2, 3, 4, 5, 10, or more seconds. As another example, the configured delay may be greater than the delay between the time the compressor is activated and the time the atomized mist first starts being output from the atomizer, because it may be desirable to allow at least some of the atomized mist to be output from the atomizer before activating the fan to force the atomized mist into the adjacent environment. For example, the configured delay may in some embodiments be more than the known or derivable delay by at least 0.100, 0.250, 0.500, 0.750, 1, 2, 3, 4, 5, 10, or more seconds. Similarly, there may be a known or derivable delay between the time the compressor is deactivated and the time atomized mist stops being expelled from the outlet of the atomizer. In some configurations, such a delay may be approximately or equal to, for example, 0.250, 0.500, 0.750, 1, 2, 3, 4, 5, 6, 7, 8, 9, 10, 20, 30, or more seconds. In some configurations, such a delay may be within a range bounded by any of the above numbers. The controller in some systems may be configured to first deactivate the compressor, and then delay for that period of time, or for a period of time having a relationship to that period of time, before deactivating the fan. For example, the configured delay may be greater than the delay between the time the compressor is deactivated and the time the atomized mist stops being output from the atomizer, because it may be desirable to keep the fan activated for a certain period of time after atomized mist has completed being expelled from the atomizer, such as to help dry the outlet of the atomizer to further reduce buildup or residue over time on the outlet of the atomizer. For example, the configured delay may in some embodiments be more than the known or derivable delay by at least 0.100, 0.250, 0.500, 0.750, 1, 2, 3, 4, 5, 10, 20, 30, or more seconds.

Another example of how power savings may be achieved is that the dispenser may include one or more sensors configured to detect one or more environmental parameters that can be used to automatically adjust a timing, duration, speed, and/or the like in dispensing atomized fragrance. For example, the dispenser may include a motion sensor, light sensor, occupancy sensor, and/or other type of sensor that detects the presence of individuals in the surrounding area. As another example, the dispenser may include a volatile organic compounds (VOCs) sensor and/or other type of sensor that detects an amount of fragrance or other compound remaining in the air. In addition to power savings, such features could be used to also save fragrance, such as by not dispensing fragrance when no individuals are around to smell it.

Some embodiments may operate in different modes depending on whether the device is currently battery-powered or powered from an AC power source. For example, a system that is currently battery-powered may be configured to utilize less power than a system that is currently powered from an AC power source, such as in order to extend the battery life. Such a power-saving configuration may include extending a duration between dispensings, reducing a fan speed, disabling a heat source, and/or the like.

Various embodiments may provide the forced air that disperses the atomized mist in various ways. For example, a fan may be positioned adjacent to the outlet of the atomizer and directly apply a flow of air to the atomized mist exiting the atomizer. For example, the fan may be positioned no more than 1, 2, 3, 4, 5, 6, 7, 8, 9, 10, 15, 20, 25, 30, 35, 40, 45, or 50 mm away from the outlet of the atomizer. As another example, a distance between the fan and the outlet of the atomizer may be within a range bounded by any of the above numbers. As another example, a distance between the fan and the outlet of the atomizer may be no greater than a diameter of the fan's rotor. As another example, a ducted fan may be used, with the exit of the duct or some other portion of the duct being exposed to the outlet of the atomizer. Further, in some embodiments, the same compressed air source that is used to power the atomizer may also be used to provide a source of air that helps to disperse the atomized mist. For example, one tube may fluidly couple the air compressor with the atomizer, while a second tube may fluidly couple the air compressor to an area adjacent the outlet of the atomizer. Some embodiments may include one or more solenoid valves and/or the like to direct the compressed air to the atomizer, the outlet, and/or the like.

It should be noted that, although much of the disclosure provided herein describes dispensing of a volatile liquid such as a fragrance, the techniques and systems disclosed herein are not limited to only dispensing fragrance. For example, the techniques and systems disclosed herein could be used to dispense a sanitizer, a cleaner, a fragrance, a combination thereof, and/or the like. Accordingly, any embodiment disclosed herein that is described with reference to dispensing fragrance could also or alternatively be used to dispense other types of volatile liquids.

Example Dispenser

Figure 1A:
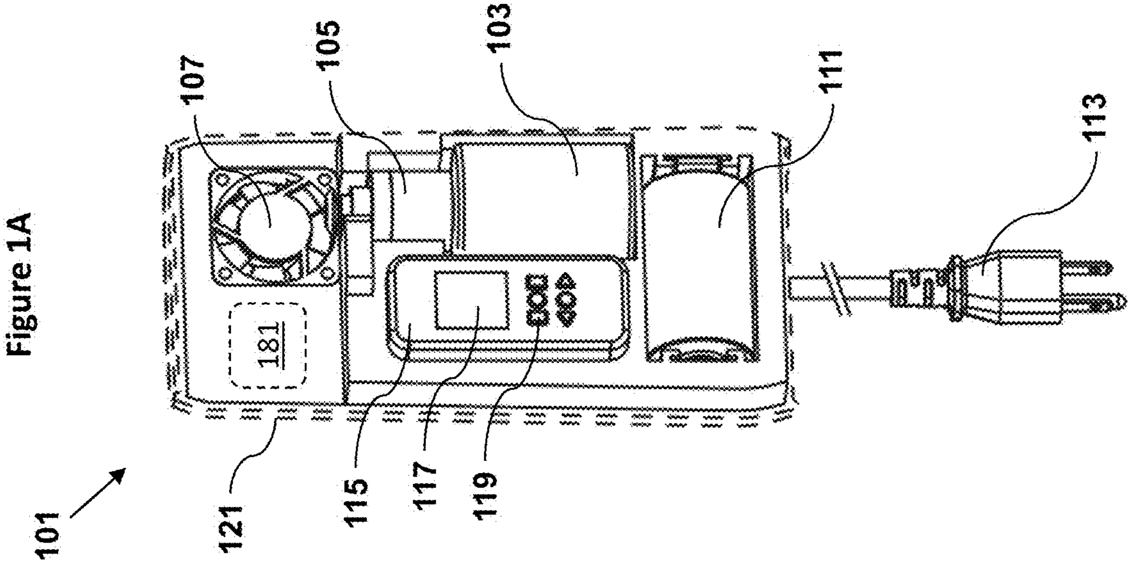
FIG. 1A is a perspective view of an embodiment of a fragrance dispenser, with certain components hidden to illustrate internal features.

FIGS. 1A and 1B illustrate an example embodiment of a dispenser 101. These figures illustrate a perspective view of the dispenser 101 with certain components hidden, such as portions of the housing 121, in order to illustrate internal features. The dispenser 101 includes a bottle, container, chamber, reservoir, and/or the like 103 for holding a supply of liquid fragrance, other volatile liquid, and/or the like. The bottle 103 is coupled to an atomizer or actuator 105 that is configured to selectively extract liquid fragrance from the bottle 103 and atomize it into a mist. Further details of how such an atomizer 105 can work are described below with reference to FIGS. 2A and 2B.

With continued reference to FIG. 1A, the dispenser 101 further comprises a fan 107 that can be used to disperse the atomized mist of fragrance output by the atomizer 105. For example, as shown in FIG. 1B, and atomized fragrance mist 123 is being output from the atomizer 105, and a more dispersed atomized fragrance 124 is being directed away from the atomizer 105 by a flow of air produced by the fan 107. This embodiment illustrates a square axial fan positioned adjacent to the output of the atomizer 105 in order to disperse the atomized fragrance. Any other suitable source of forced air (and/or other gas) may be used in certain embodiments. For example, a centrifugal fan may be used in place of axial fan. As another example, a fan, such as an axial fan or a centrifugal fan, may be positioned elsewhere in the housing 121 and connected to a duct that supplies forced air from the fan to an area adjacent the outlet of the atomizer 105. In some embodiments, the fan may desirably be an axial flow flan that can generate a flow rate of at least 300 $ft.^3$ per minute and/or over 600 $ft.^3$ per minute. In some embodiments, the fan can create a flow rate of 300 to 1000 $ft.^3$ per minute. In some embodiments, the fan can create a flow rate of at least 200, 300, 400, 500, 600, 700, 800, 1000, or more cubic feet per minute. In some embodiments, the fan can create a flow rate within a range bounded by any two of the above numbers. The fan may in some embodiments desirably rotate over 500 revolutions per minute and/or over 1000 revolutions per minute. In some configurations, the fan can rotate between 500-5,000 revolutions per minute. In some configurations, the fan can rotate at a speed of at least 250, 500, 750, 1000, 1250, 1500, 1750, 2000, 2250, 2500, 2750, 3000, 3250, 3500, 3750, 4000, 4250, 4500, 4700, 5000, or more revolutions per minute. In some configurations, the fan can rotate at a speed that is within a range bounded by any two of the above numbers. In some embodiments, a relatively large diameter fan may be utilized in order to obtain a similar flow rate at a lower rotational speed, thus potentially reducing the noise level of the unit during operation. Potential fan sizes include, but are not limited to, 25 mm, 30 mm, 40 mm, 50 mm, 60 mm, 70 mm, 80 mm, 90 mm, 100 mm, 110 mm, 120 mm, and or the like. These sizes refer to the nominal fan size (e.g., the edge-to-edge measurement of a square fan, as used with commercially available computer case fans and the like). Alternatively, a fan may be used that comprises a rotor diameter within a range bounded by any two of the above numbers. Further, although the drawings illustrate static fans that do not move with respect to the housing (other than the rotation of the rotor), one or more moving fans, such as oscillating fans may be used with any embodiment disclosed herein. Using an oscillating fan may be beneficial, for example, such as to assist in distribution of the atomized materials over a wider area. In some embodiments, one or more static fans may be used, and the housing or some other component of the system that the fan is connected to may be configured to move, oscillate, rotate, and/or the like. Some embodiments may include more than one fan, static and/or oscillating, in order to help distribute atomized materials over a wider area.

Having a system with increased distribution of atomized materials can be beneficial in many situations, and particularly in situations where active materials, such as sanitizers, are being distributed. For example, systems as disclosed herein could be used in various situations where sanitization of an area is required. For example, a trailer that transports food or livestock may need to be sanitized before use. One or more of the systems disclosed herein could be placed within such a trailer and used to sanitize the trailer before use. The various techniques disclosed herein, including utilizing one or more venturi atomizers to atomize a volatile liquid and increasing distribution of the atomized liquid using a fan, can allow for higher dosing levels in such a situation than other micro-diffuser technologies (such as heat-based micro-diffusers, ultrasonic-based micro-diffusers, and/or the like). As described elsewhere herein, however, heat, ultrasonic, and/or other technologies may still be used with the techniques disclosed herein and/or combined with the techniques disclosed herein.

Returning to FIGS. 1A and 1B, the dispenser 101 may further comprise a compressor pump, such as compressor 109 of FIG. 2A described below, and/or another source of compressed air that can supply compressed air to the atomizer 105. Such a compressor is not shown in FIGS. 1A and 1B but could, for example, be positioned behind the controller 115 (described below).

The dispenser 101 further comprises one or more sources of electrical energy. For example, the dispenser 101 may comprise a battery 111, an electrical connector plug 113 configured to plug into an AC electrical outlet, and/or the like. The source or sources of electrical energy may be used to power, for example, a compressor, the fan 107, the controller 115, and/or the like.

With continued reference to FIG. 1A, the dispenser 101 comprises a controller 115 that comprises a display or screen 117 and a plurality of user inputs 119 (such as, for example, buttons, switches, and/or the like). The controller 115 may be configured to activate and deactivate the various electromechanical components of the dispenser 101, such as the fan 107, a compressor (such as compressor 109 of FIG. 2A), and/or the like. The controller 115 may further be configured to control one or more parameters of operation of devices such as the fan 107 and compressor 109. For example, the controller 115 may be configured to control the speed, voltage level, current draw, duration of activation, and/or the like. The controller 115 may further be configured to control when the various devices activate and/or deactivate, operating parameters of the devices such as speed, voltage level, current draw, and/or the like, based on one or more trigger events. For example, one trigger event may be a timer that causes the controller to activate the system on a set time or at set intervals. As another example, a trigger event may comprise detecting motion in an area, a certain period of time passing from the last motion detection, detecting a threshold level of volatile organic compounds (VOCs) in the air around the dispenser, detecting a threshold level of light in the area, and/or the like. Such trigger events may involve the controller 115 communicating with one or more sensors, indicated by block 181 of FIGS. 1A and 1B. Example sensors may include motion sensors, light sensors, occupancy sensors, and/or other types of sensors that detect the presence of individuals in the surrounding area. Other example sensors may include VOC sensors and/or other types of sensors that detect an amount of fragrance or other compound in the air. Although the embodiment of FIG. 1A is described as including one or more sensors 181, some embodiments may not include such sensors.

The display 117 and user inputs 119 of the controller 115 can be configured to enable a user to configure one or more parameters of the controller 115 and/or to provide certain information or feedback to the user. For example, the display 117 and user inputs 119 may enable a user to adjust one or more of the parameters discussed above, such as interval timing, duration, motion detection, VOCs detection, a desired level of fragrance to maintain in the area, light detection, and/or the like. The display 117 may further be configured to indicate to a user an amount of fragrance remaining in the system, an estimated time until the fragrance needs to be refilled, a battery level, the time remaining until the next dispense, and/or the like.

Although the embodiment of FIGS. 1A and 1B includes a controller 115 with features that provide feedback to a user and/or allow a user to configure the system, other embodiments may not include some or all of these features. For example, a system may include a controller that uses one or more of the above discussed parameters to control the system, but may not be end-user configurable. Further, some embodiments may allow user configuration through different means, such as a connection to the dispenser from a computer or smartphone using a USB cable, a BLUETOOTH connection, and/or the like.

In the embodiment of FIGS. 1A and 1B, the housing 121 is depicted as a series of dashed lines generally encompassing the various elements of the dispenser 101. The housing 121 may take a variety of forms, including, for example, a plastic, metal, or other type of housing shaped and configured to be mounted to a wall, placed on a desk, placed on the floor, mounted to a ceiling, and/or the like. Further, the housing 121 may comprise one or more openings, grates, screens, and/or the like positioned in the airflow stream generated by the fan 107 in order to allow the dispersed atomized fragrance to exit the housing 121. The housing 121 may further comprise one or more openings, grates, screens, and/or the like positioned upstream of the fan 107 to act as in inlet for environmental air to be sucked into the housing 121 by the fan 107. The housing 121 may further comprise one or more removable and/or openable panels that enable a user to access the battery 111 and/or bottle 103 for replacement.

Although an AC plug and cord 113 is depicted in FIGS. 1A and 1B, some embodiments may not include such a electrical plug and cord, and may be powered only by the battery 111 or other self-contained power source. Further, some embodiments may include the AC electrical plug 113 and may not include a battery 111 or other self-contained source of power. Further, some embodiments may utilize a rechargeable power source, such as a lithium-ion battery, and such battery may or may not be configured to be user replaceable.

Additional Dispenser Example

Figure 2B:
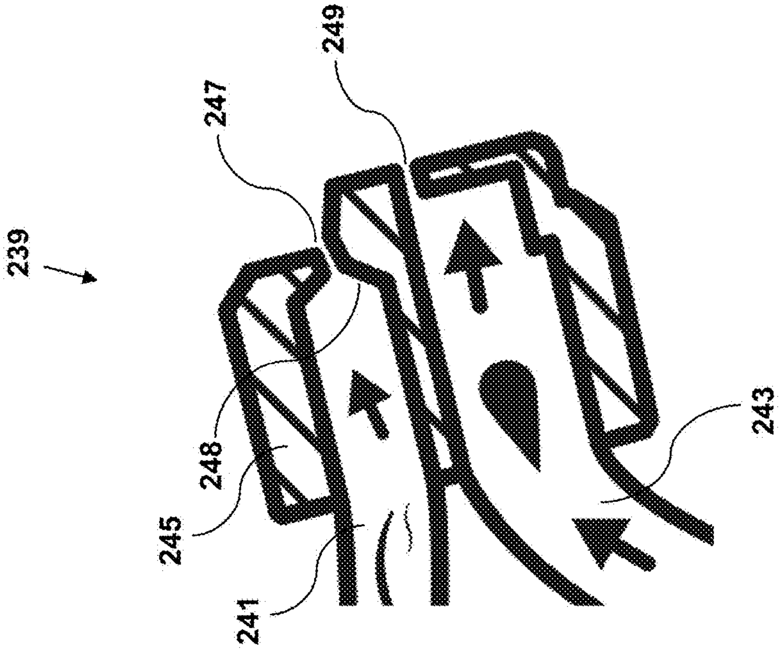
FIG. 2B is an enlarged cross-sectional view of a venturi assembly of the fragrance dispenser of FIG. 2A.
Figure 2A:
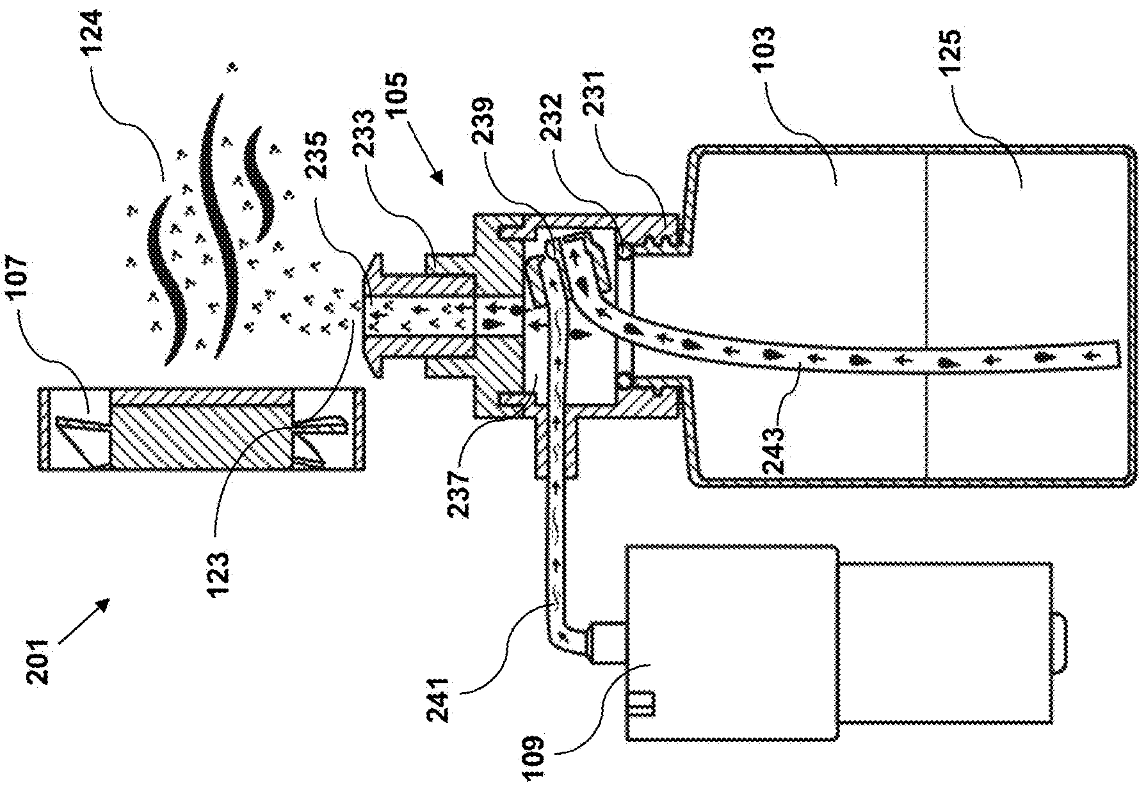
FIG. 2A is a side partial cross-sectional view of another embodiment of a fragrance dispenser, with certain components hidden to illustrate internal features.

FIGS. 2A and 2B illustrate further internal details of a dispenser 201. FIG. 2A is a side partial cross-sectional view of the dispenser 201, and FIG. 2B is an enlarged cross-sectional view of a portion of FIG. 2A. The dispenser 201 includes a bottle 103, atomizer 105, and fan 107 similar to the embodiment of FIGS. 1A and 1B. The dispenser 201 further comprises a compressor pump 109 that may be included in the embodiment of FIGS. 1A and 1B but is not shown in FIGS. 1A and 1B. The dispenser 201 may comprise various other features, such as the various other features described above with respect to dispenser 101, but only certain features are illustrated in FIG. 2A in order to highlight certain features of the dispenser 201.

FIG. 2A illustrates additional internal details of an atomizer 105 that can be used with any embodiment disclosed herein. Specifically, the atomizer 105 comprises a first end 231 to which the bottle 103 containing liquid fragrance 125 is coupled, and a second end 233 to which the outlet nozzle or orifice 235 is connected. The first end 231 may be configured to allow the bottle 103 to be removably coupled to the atomizer 105, such as by using a threaded connection or the like. In some embodiments, an O-ring 232 or other sealing member is also included to limit leaking of liquid fragrance 125 from the system.

The atomizer 105 further defines an internal chamber 237 in which a venturi assembly 239 is positioned. With reference to both FIGS. 2A and 2B, the venturi assembly 239 comprises a body 245 having a first nozzle or orifice 247 and a second nozzle or orifice 249. The first nozzle or orifice 247 is fluidly coupled to a tube 241 that is also fluidly coupled to the compressor 109. The first nozzle or orifice 247 is adjacent a tapered region 248 that creates a venturi effect when compressed air is passed from the compressor 109, through the tube 241, and out the first nozzle 247. This venturi effect desirably causes a reduction in pressure near second nozzle or orifice 249 that draws some of the liquid fragrance 125 through tube 243 and out the venturi assembly 239 through the second nozzle 249. The fragrance 125 is then desirably entrained with the compressed air as the compressed air flows through the chamber 237 and out the outlet nozzle or orifice 235. Due to the reduction in pressure caused by the venturi effect and the relatively high volatility of the liquid fragrance 125, the liquid fragrance 125 is caused to atomize into a mist as it passes through the second nozzle 249, into chamber 237, and out the outlet nozzle or orifice 235. The atomized mist 123 exiting the outlet nozzle 235 is desirably then dispersed into the surrounding environment as a more dispersed atomized mist 124 by an airflow generated by fan 107.

Although FIGS. 2A and 2B illustrate one specific example of utilizing a venturi effect to extract and atomize liquid fragrance from a reservoir, various other designs may be used to accomplish a similar venturi effect. For example, the first orifice 247 may not need to be part of the same body 245 as second orifice 249. As another example, the body 245 may be integrated into the main housing of the atomizer 105 instead of being positioned within the chamber 237.

Further, other methods of extracting and/or atomizing the liquid fragrance 125 may be utilized. For example, a heating mechanism may be included to atomize and/or to assist in atomizing the liquid fragrance 125. As another example, an ultrasonic mechanism may be included to atomize and/or to assist in atomizing the liquid fragrance 125. For example, one or more of the atomization element 183 of FIG. 3A (which may comprise a heating element, an ultrasonic element, and/or the like) may be included in any of the embodiments disclosed herein.

The embodiments of FIGS. 1A-2B illustrate versions where the outlet nozzle 235 is directed in a substantially upward direction, and the fan 107 is configured to generate an airflow oriented generally perpendicularly to the flow from the outlet nozzle 235 (in this case, horizontally). Other configurations may be utilized, however, including but not limited to the configuration described below with reference to FIGS. 3A and 3B, which positions the atomizer's outlet in a horizontal direction and the fan's airflow in a vertical direction. The flows from the atomizer and the fan do not necessarily always need to be perpendicular to each other; however, testing has shown such an arrangement to be an efficient way to disperse the atomized mist.

Example Alternative Dispenser

Figure 3B:
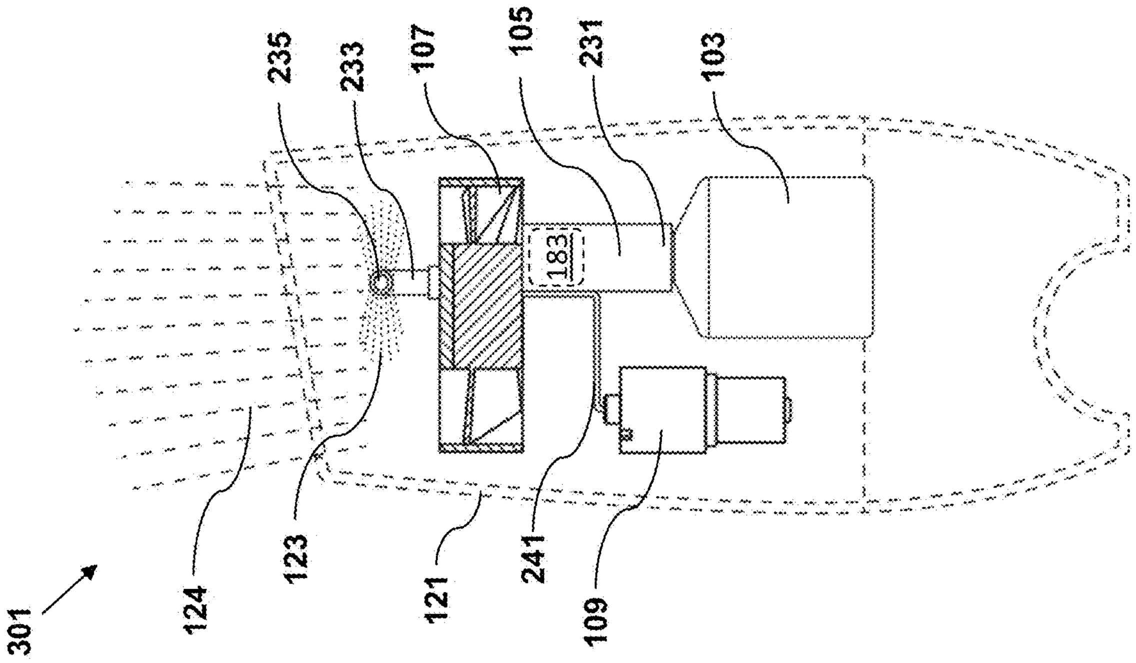
FIG. 3B is a front view illustrating the fragrance dispenser of FIG. 3A dispersing an atomized fragrance.
Figure 3A:
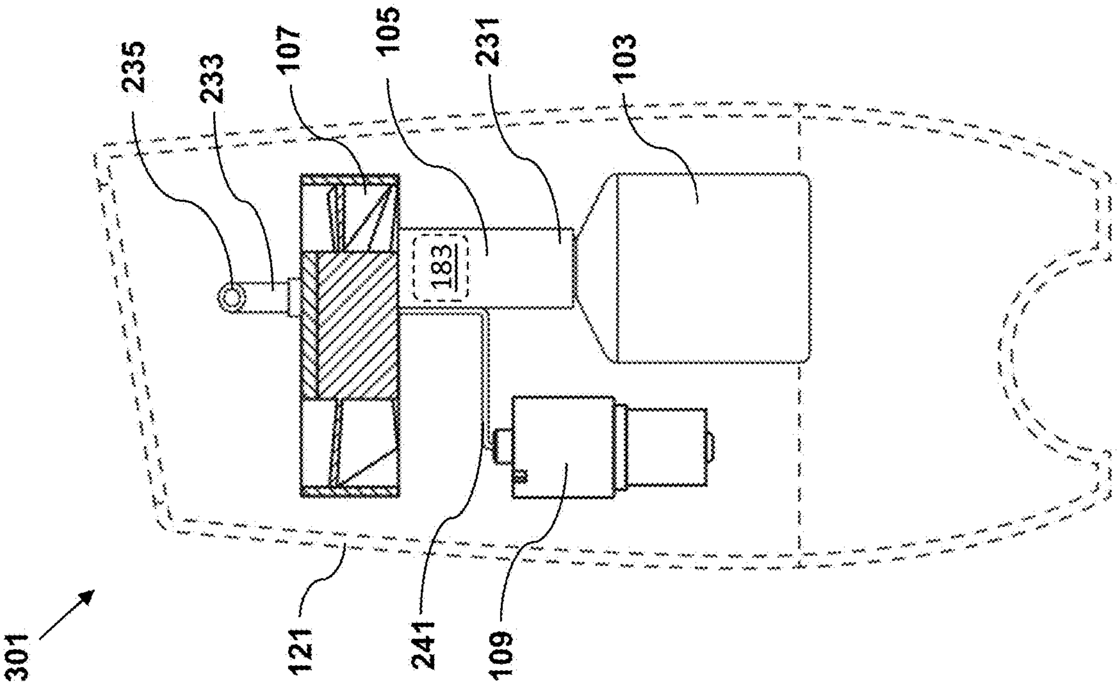
FIG. 3A is a front view of another embodiment of a fragrance dispenser, with certain components hidden to illustrate internal features.

FIGS. 3A and 3B illustrate another embodiment of a dispenser 301. The dispenser 301 is similar in many respects to the dispensers 101 and 201 discussed above, and the same or similar reference numbers are used to refer to the same or similar features. For example, the dispenser 301 comprises a bottle 103 for storing a supply of liquid fragrance, an atomizer or actuator 105, a fan 107, a compressor 109, a tube 241 connecting the compressor 109 to the atomizer 105, and a housing 121.

One difference in the dispenser 301 is that the atomizer 105 is taller and comprises a differently oriented outlet nozzle or orifice 235. Instead of the outlet nozzle 235 being directed upwardly or vertically, the outlet nozzle 235 is directed sideways or horizontally. With reference to FIG. 3B, the outlet 235 is directed toward the viewer (perpendicular to the plane of the page) and is configured to cause the atomized mist 123 output from the atomizer 105 to be directed in a generally horizontal fashion.

Another difference in the dispenser 301 is that the fan 107 is positioned to generate a flow of air in a generally upward or vertical direction instead of a generally sideways or horizontal direction. Accordingly, the atomized mist 123 output from the atomizer 105 is caused to be disbursed generally upward as shown by dispersed atomized mist 124. Such a configuration may be more desirable for a dispenser that is intended to be positioned away from a wall of a room (such as positioned on a table or desk), while the configuration of dispenser 101 may be more desirable for a dispenser that is intended to be positioned next to a wall, such as mounted on a wall of a room, bathroom, office space, and/or the like.

Another difference in the dispenser 301 is that an optional atomization element 183 is included in the atomizer 105. The atomization element 183 may comprises, for example, a heating element, an ultrasonic element, and/or the like that helps to atomize the liquid fragrance. Such an atomization element 183 is not required, however.

It should be noted that, although the embodiment of FIGS. 3A and 3B does not illustrate a source of power, a controller, or a user interface, any of such features may be incorporated into the dispenser 301.

Example Dispensing Method

Figure 4:
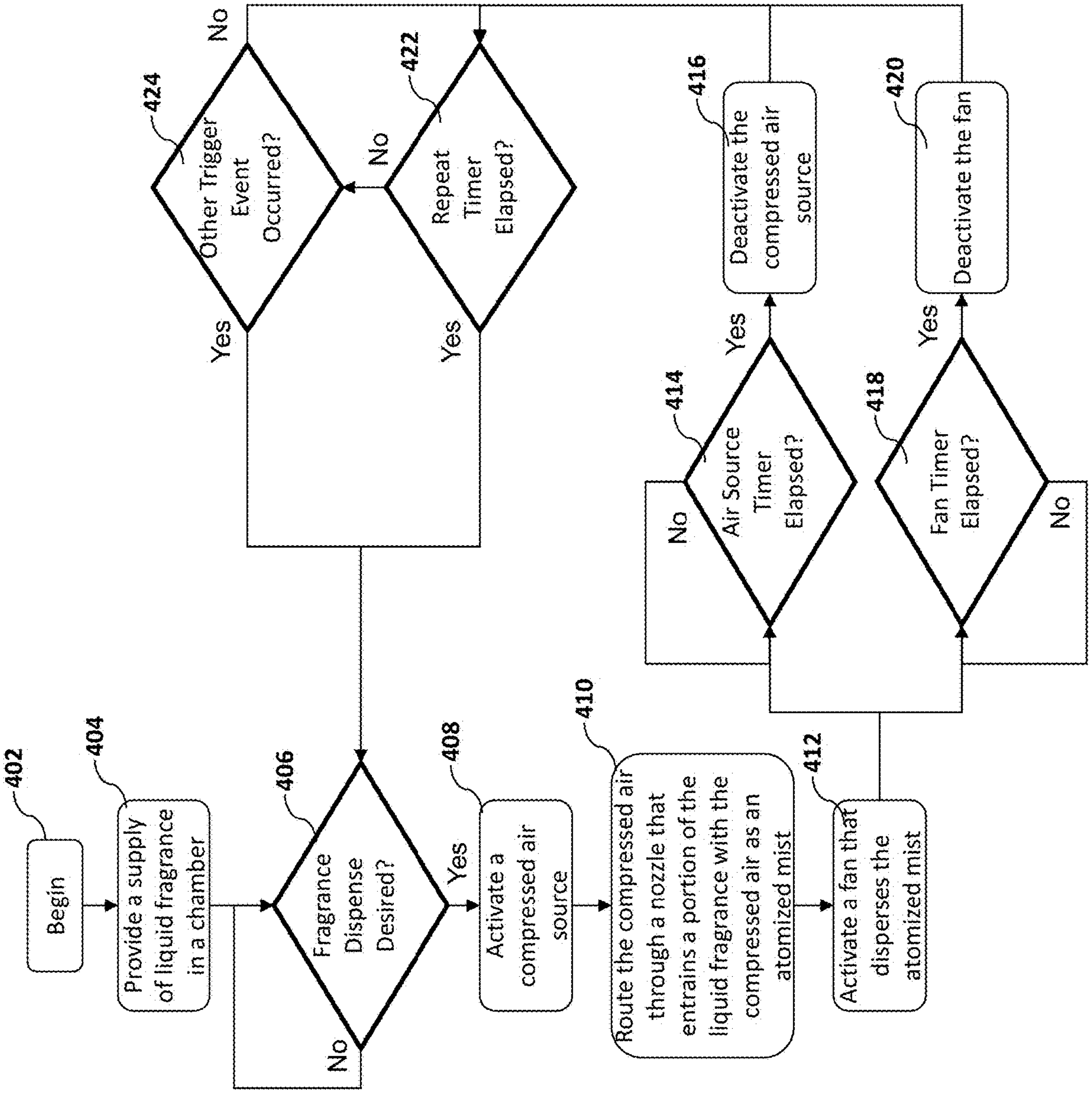
FIG. 4 is a process flow diagram depicting an embodiment of a process for dispensing fragrance.

FIG. 4 illustrates an example embodiment of a process flow diagram that may be implemented by any of the dispensing systems disclosed herein. This process flow diagram depicts merely one specific example of how such a dispensing system can operate, and the systems and techniques disclosed herein may also operate in various other ways.

The process flow begins at block 402. At block 404, a supply of liquid fragrance is provided in a chamber. For example, the bottle 103 of FIG. 2A may be provided. At block 406, the process flow varies depending on whether a fragrance dispense is desired. For example, the system may be configured to sit idle for extended periods of time, and only dispense fragrance at set intervals, in response to some other trigger event, in response to a manual request via a user input, and/or the like. If a fragrance dispense is desired at block 406, the process flow proceeds to block 408. At block 408, a source of compressed air is activated. For example, a controller may activate the compressor 109 of dispenser 201 of FIG. 2A. Alternatively, a different source of compressed air may be used.

At block 410, the compressed air generated by the compressed air source is routed through a nozzle that entrains a portion of the liquid fragrance with the compressed air as an atomized mist. For example, the compressed air may be routed through tube 241 of FIG. 2A, and through the venturi assembly 239, thus leading to extraction of a portion of liquid fragrance 125 through the second nozzle 249, and entraining the fragrance with the compressed air as an atomized mist. At block 412, a fan is activated to disperse the atomized mist. For example, the fan 107 of FIG. 2A may be activated to cause an airflow that disperses atomized mist 124.

In some embodiments, one or more timers may be used to control how long the compressed air source and or fan are activated. In some embodiments, the compressed air source and fan may be deactivated simultaneously. In the embodiment illustrated in FIG. 4, however, separate timers are used, such as to enable the compressed air source to be disabled prior to the fan, in order to help disperse any remaining atomized mist that continues to exit the atomizer after the compressed air source has been deactivated. This can also help to reduce or prevent buildup or residue on the atomizer outlet. In some embodiments, the system may be configured to continue running the fan after the compressor has been deactivated for a certain amount of time. Such amount of time may be, for example, 0.1 seconds, 0.25 seconds, 0.5 seconds, one second, two seconds, three seconds, four seconds, five seconds, six seconds, seven seconds, eight seconds, nine seconds, 10 seconds, or more. Such amount of time may in some embodiments be within a range bounded by any of the above numbers. Further, although not depicted in the embodiment of FIG. 4, some embodiments may incorporate a time delay that delays activation of the fan a certain amount of time after activating the compressed air source. Such amount of time may be, for example, 0.1 seconds, 0.25 seconds, 0.5 seconds, one second, two seconds, three seconds, four seconds, five seconds, six seconds, seven seconds, eight seconds, nine seconds, 10 seconds, or higher. Such amount of time may in some embodiments be within a range bounded by any of the above numbers.

With continued reference to FIG. 4, at block 414 the process flow varies depending on whether the compressed air source timer has elapsed. If the compressed air source timer has elapsed, the process flow proceeds to block 416 and the compressed air source is deactivated. At block 418, the process flow varies depending on whether the fan timer has elapsed. If the fan timer has elapsed, the process flow proceeds to block 420 and the fan is deactivated. The process flow then proceeds to block 422 wherein the process flow varies depending on whether a repeat or interval timer has elapsed. If the repeat or interval timer has elapsed, the process flow proceeds back to block 406 and proceeds as described above. If the repeat or interval timer has not elapsed at block 422, the process flow proceeds to block 424. At block 424, the process flow varies depending on whether any other trigger event has occurred. For example, another trigger event may comprise a motion detection, a level of light detection, a detection of a level of VOCs in the environment, a request via a user input to manually trigger a fragrance dispense, and/or the like. If a trigger event has occurred, the process flow proceeds from block 424 back to block 406, and proceeds as discussed above.

As discussed above, the process flow illustrated in FIG. 4 is merely an example, and other processes for using the systems and techniques disclosed herein may not include each of the blocks of FIG. 4, may add additional blocks, may replace one or more blocks with alternate blocks, may combine one or more blocks into a single block, and/or the like.

Example Alternative Dispenser

Figure 5:
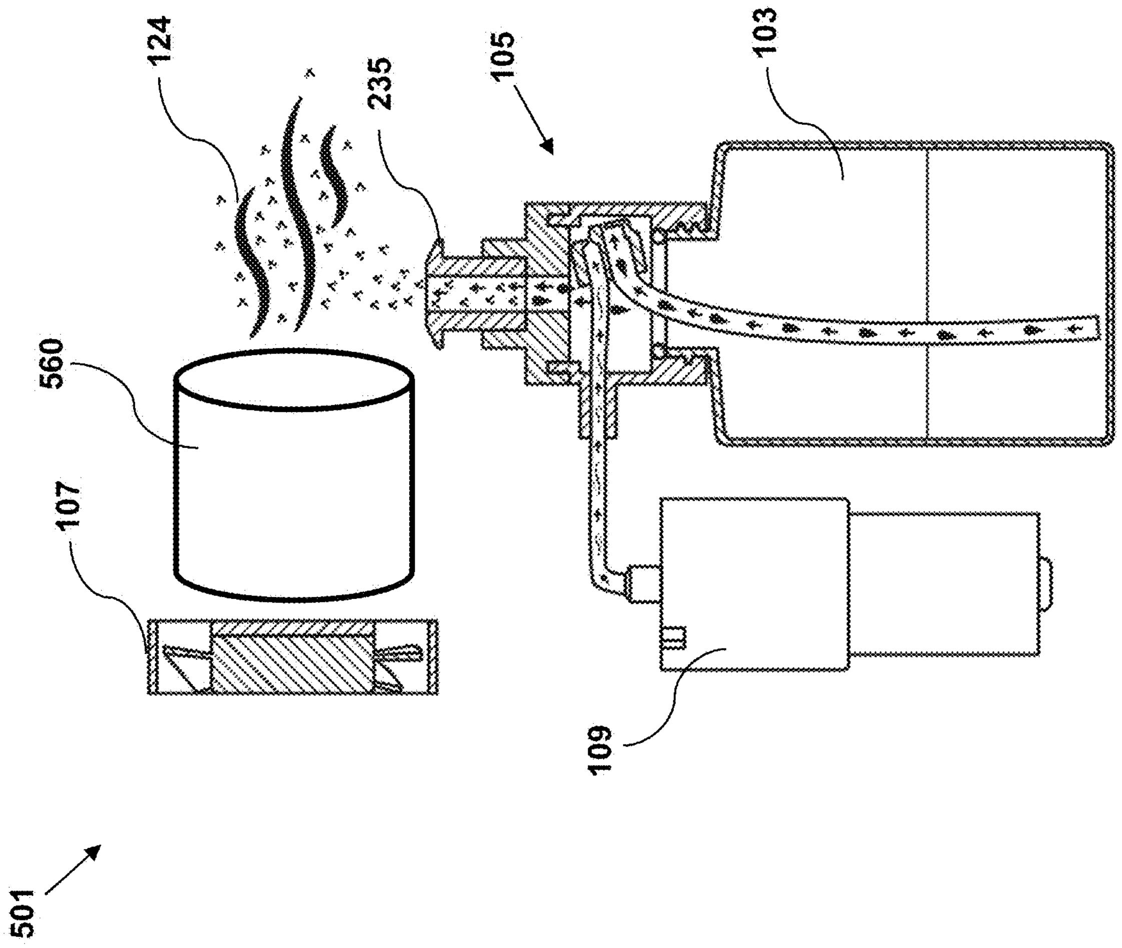
FIG. 5 is a side partial cross-sectional view of another embodiment of a fragrance dispenser that includes a ducted fan, with certain components hidden to illustrate internal features.

FIG. 5 illustrates another embodiment of a dispenser 501. The dispenser 501 is similar to the dispenser 201 illustrated in FIG. 2A and can include the same or similar components and operate in the same or similar fashion as dispenser 201. One difference in the dispenser 501 is that the fan 107 is not positioned adjacent to the outlet nozzle 235 of the atomizer 105. Instead, a duct 560 is positioned between the fan 107 and an area adjacent the outlet nozzle 235, in order to direct an airflow generated by the fan 107 to the area adjacent the outlet nozzle 235. Such a configuration may be desirable for a number of reasons, such as for packaging reasons that enable the fan to more efficiently fit at a different portion of the housing, for noise and/or aesthetic reasons, and/or the like. For example, it may be desirable to utilize a larger diameter fan that produces less noise than a smaller diameter fan at the same airflow rate, and packaging reasons may make it desirable to position that larger fan somewhere other than next to the atomizer outlet.

Although the embodiment of FIG. 5 illustrates the fan 107 as directing its airflow horizontally, other embodiments may position the fan 107 differently, such as directing its airflow vertically or any other direction between horizontal and vertical. The duct 560 may then be used to redirect the airflow output by the fan 107 into a different direction, if desired. For example, if it is desired for the airflow to be generally perpendicular to the outlet nozzle 235, the duct 560 may be configured to redirect the airflow from the fan 107 into that direction, regardless of the direction the fan 107 is facing.

In some embodiments, the duct 560 could alternatively be coupled to the compressor 109, and the dispenser may not include a fan 107. Further, in some embodiments, one or more valves, solenoid valves, one-way valves, and/or the like may be configured to direct an output from the compressor 109 to the atomizer 105, the duct 560, or a combination of the two.

In some embodiment, a duct may additionally or alternatively be positioned upstream of the fan 107, such as between the fan 107 and an air inlet in the housing.

Additional Example Alternative Dispenser

Figure 6:
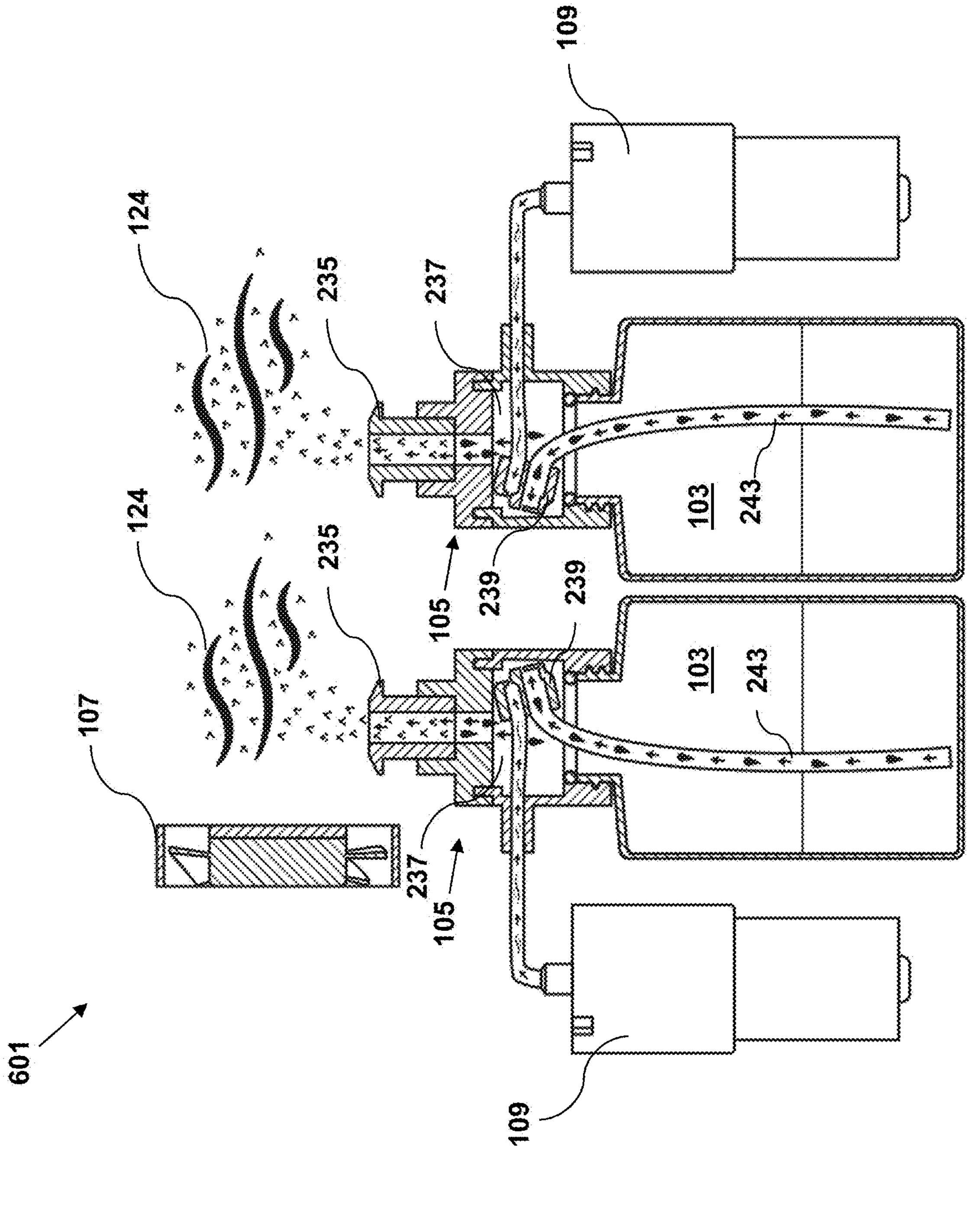
FIG. 6 is a side partial cross-sectional view of another embodiment of a volatile liquid dispenser, with certain components hidden to illustrate internal features.

FIG. 6 illustrates another embodiment of a dispenser 601. The dispenser 601 is similar to the dispenser 201 of FIG. 2A, except that the dispenser 601 is configured to dispense a plurality of volatile liquids. For example, the dispenser 601 includes two liquid chambers 103 each coupled to an atomizer 105 and a pressurized gas source such as a compressor 109. This embodiment includes a single fan 107 configured to disperse the atomized mist output from each of the atomizers 105, but some embodiments could include a different number of fans, such as a separate fan for each atomizer.

A dispenser that includes the ability to dispense more than one volatile liquid can be beneficial for a number of reasons. For example, it may be desirable to be able to dispense a fragrance from one chamber and to dispense an active material, such as a sanitizer, from another chamber. In some embodiments, the multiple volatile liquids may be configured to be dispensed simultaneously, while other embodiments may be configured to selectively dispense one or more of a subset of a total number of volatile liquids stored in the dispenser.

Although FIG. 6 illustrates an embodiment that can dispense two different liquids using two different atomizers 105, various other arrangements may be used. For example, any number of liquid chambers 103 and atomizers 105 may be included in a dispenser. Further, any number of pressurized gas sources may be included, and some embodiments may have less pressurized gas sources than the number of liquid chambers 103, such as because the system may be configured to share one or more pressurized gas sources among two or more of the atomizers 105.

Additionally, although the embodiment of FIG. 6 illustrates a system that uses a different atomizer 105 for each liquid chamber 103, some systems may combine two or more liquids from separate chambers in a single atomizer 105. For example, the system may include a separate tube 243 going into each liquid chamber 103, but the tubes 243 may each lead to the same atomizer 105. In some embodiments, each separate tube 243 may still lead to separate venturi assemblies 239, but the separate venturi assemblies 239 may be positioned to output volatile liquid into the same atomizer chamber 237. Such a configuration could be desirable, for example, such as to enable in-nozzle mixing of materials from two or more liquid chambers. Stated another way, such a system could allow for the in-situ blending of materials that otherwise may not be compatible and/or stable with one another over periods of time if, for example, such materials were pre-blended and stored within the same liquid chamber. In some embodiments, instead of having multiple venturi assemblies 239 within the same chamber 237, a single venturi assembly 239 may be configured to be coupled with multiple tubes 243 each leading to a different chamber 103.

Additional Embodiments

Any embodiment disclosed herein may be modified to include one or more valves, solenoid valves, check valves, one-way valves, and/or the like. For example, one or more check valves may be used in or fluidly coupled to the tubes 241 and/or 243 of FIG. 2A and/or the duct 560 of FIG. 5. Such valves may be used to, for example, increase the predictability of operation of the system, selectively fluidly couple or decouple one component from another, and/or the like.

Any embodiment disclosed herein may also be modified to include one or more heating device and/or ultrasonic device that operates to atomize the volatile liquid and/or helps to atomize the volatile liquid. For example, the atomizer 105 of any of the embodiments discussed above may include one or more heating elements and/or ultrasonic elements.

From the foregoing description, it will be appreciated that embodiments of an inventive dispenser are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations and/or "some embodiments" can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures, or at least some portions of the figures, may be drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A volatile liquid dispensing system comprising:
- a reservoir for holding a supply of volatile liquid;
- a pressurized gas source;
- an atomizer comprising a chamber, an outlet nozzle fluidly coupleable to the chamber, and a venturi assembly positioned within the chamber,
- wherein the venturi assembly comprises a first orifice fluidly coupleable to the pressurized gas source through a flow path that includes a venturi nozzle, and a second orifice fluidly coupleable to the reservoir,
- wherein the atomizer is configured to cause, responsive to pressurized gas from the pressurized gas source flowing through the venturi nozzle, extraction of a portion of the supply of volatile liquid through the second orifice, atomization of the portion of the supply of volatile liquid within the chamber and/or the outlet nozzle, and expelling of the atomized liquid through the outlet nozzle;
- an electrical power source;
- a fan configured to be powered by the electrical power source in order to generate a flow of air;
- a duct positioned to transfer the flow of air from the fan to an exit of the duct that is positioned adjacent the outlet nozzle, such that the flow of air exiting the duct can be applied to the atomized liquid expelled through the outlet nozzle to disperse the atomized liquid;
- a controller configured to repeatedly automatically activate and deactivate the pressurized gas source and the fan such that, responsive to a trigger event occurring, the controller will implement a dispensing process that causes:
  - activation of both the pressurized gas source and the fan, to atomize the portion of the supply of volatile liquid and to disperse the atomized liquid;
  - deactivation of the pressurized gas source while keeping the fan activated for a period of time, to continue dispersing the atomized liquid after the compressed gas source has been deactivated; and
  - deactivation of the fan after the period of time,
- wherein the controller is configured to repeat the dispensing process responsive to an additional trigger event occurring,
- wherein the trigger event and the additional trigger event each comprises at least one of a timer elapsing, a motion detection, or a light detection; and
- a housing that contains at least the controller, the reservoir, the pressurized gas source, the atomizer, the fan, and the duct.

2. The volatile liquid dispensing system of claim 1, wherein the pressurized gas source comprises a compressor configured to be powered by the electrical power source.

3. The volatile liquid dispensing system of claim 1, wherein the pressurized gas source comprises a chamber containing pressurized fluid.

4. The volatile liquid dispensing system of claim 1, wherein the electrical power source comprises a battery.

5. The volatile liquid dispensing system of claim 1, wherein the electrical power source comprises a connection to receive power from an external AC power source.

6. The volatile liquid dispensing system of claim 1, wherein the fan can create a flow rate of 300-1000 cubic feet per minute.

7. The volatile liquid dispensing system of claim 1, wherein the trigger event comprises a timer elapsing.

8. The volatile liquid dispensing system of claim 1, wherein the period of time is at least two seconds.

9. The volatile liquid dispensing system of claim 1, further comprising a second reservoir for holding a supply of a second volatile liquid.

10. The volatile liquid dispensing system of claim 1, wherein the period of time is within a range of two to ten seconds.

11. The volatile liquid dispensing system of claim 1, wherein the period of time is within a range of five to ten seconds.

12. The volatile liquid dispensing system of claim 1, wherein the additional trigger event comprises a timer elapsing.

13. A volatile liquid dispensing system comprising:
- a reservoir for holding a supply of volatile liquid;
- a pressurized gas source;
- a venturi assembly comprising a first orifice fluidly coupleable to the pressurized gas source, and a second orifice fluidly coupleable to the reservoir,
- wherein the first orifice is positioned adjacent to the second orifice, such that the venturi assembly is configured to create a venturi effect, responsive to pressurized gas from the pressurized gas source flowing through the first orifice, that causes extraction and atomization of a portion of the supply of volatile liquid through the second orifice;
- an electrical power source;
- a fan configured to be powered by the electrical power source in order to generate a flow of air;
- a duct positioned to transfer the flow of air from the fan to an exit of the duct that is positioned such that the flow of air exiting the duct can be applied to the atomized liquid to disperse the atomized liquid;
- a controller configured to repeatedly automatically activate and deactivate the pressurized gas source and the fan such that, responsive to a trigger event occurring, the controller will implement a dispensing process that causes:
  - activation of both the pressurized gas source and the fan, to atomize the portion of the supply of volatile liquid and to disperse the atomized liquid;
  - deactivation of the pressurized gas source while keeping the fan activated for a period of time, to continue dispersing the atomized liquid after the compressed gas source has been deactivated; and
  - deactivation of the fan after the period of time,
- wherein the controller is configured to repeat the dispensing process responsive to an additional trigger event occurring,
- wherein the trigger event and the additional trigger event each comprises at least one of: a timer elapsing, a motion detection, or a light detection; and
- a housing that contains at least the controller, the reservoir, the pressurized gas source, the venturi assembly, the fan, and the duct.

14. The volatile liquid dispensing system of claim 13, wherein the pressurized gas source comprises a compressor configured to be powered by the electrical power source.

15. The volatile liquid dispensing system of claim 13, wherein the pressurized gas source comprises a chamber containing pressurized fluid.

16. The volatile liquid dispensing system of claim 13, wherein the electrical power source comprises a battery.

17. The volatile liquid dispensing system of claim 13, wherein the electrical power source comprises a connection to receive power from an external AC power source.

18. The volatile liquid dispensing system of claim 13, wherein the trigger event comprises a timer elapsing.

19. The volatile liquid dispensing system of claim 13, wherein the period of time is at least two seconds.

20. The volatile liquid dispensing system of claim 13, wherein the period of time is within a range of two to ten seconds.

21. The volatile liquid dispensing system of claim 13, wherein the additional trigger event comprises a timer elapsing.

22. The volatile liquid dispensing system of claim 13, wherein the additional trigger event comprises a motion detection.

23. The volatile liquid dispensing system of claim 13, wherein the additional trigger event comprises a light detection.

* * * * *